United States Patent [19]
Rink et al.

[11] Patent Number: 5,181,233
[45] Date of Patent: Jan. 19, 1993

[54] SPECIMEN HOLDER

[75] Inventors: William J. Rink; Joseph B. Schlenoff; Haim H. G. Mathias, all of Tallahassee, Fla.

[73] Assignee: Florida State University, Tallahassee, Fla.

[21] Appl. No.: 790,203

[22] Filed: Nov. 8, 1991

[51] Int. Cl.⁵ .......................................... G01N 23/20
[52] U.S. Cl. ..................................... 378/79; 378/204
[58] Field of Search .................... 378/79, 80, 81, 210, 378/204, 70, 71, 208; 250/442.11

[56] References Cited

U.S. PATENT DOCUMENTS

| | | | |
|---|---|---|---|
| 3,126,478 | 3/1964 | Götz et al. | 250/51 |
| 3,218,459 | 11/1965 | Bens | 250/51.5 |
| 3,322,948 | 5/1967 | Baak et al. | 250/51.5 |
| 3,566,112 | 2/1971 | Luecke | 250/51.5 |
| 3,600,576 | 8/1971 | Carter et al. | 250/51.5 R |
| 3,619,610 | 11/1971 | Politis | 250/51.5 |
| 3,654,460 | 4/1972 | Payton et al. | 250/51.5 |
| 3,727,052 | 4/1973 | Hino | 250/51.5 |
| 3,973,120 | 8/1976 | Kessels | 250/262 |
| 4,076,981 | 2/1978 | Sparks et al. | 250/272 |
| 4,573,182 | 2/1986 | Manners | 378/75 |
| 4,583,242 | 4/1986 | Vinegar et al. | 378/208 |
| 4,641,329 | 2/1987 | Green et al. | 378/79 |
| 4,642,811 | 2/1987 | Georgopoulos | 378/53 |
| 4,770,593 | 9/1988 | Anderson | 414/331 |
| 4,821,303 | 4/1989 | Fawcett et al. | 378/80 |
| 4,827,761 | 5/1989 | Vinegar et al. | 378/208 |

OTHER PUBLICATIONS

Author: Rigaku; Title: X-Ray Diffractometer Attachments; pp. 1, 3, 5, 7 and 8.
Author: Anton Paar K. G.; Title: High-Temperature Attachment for X-Ray Diffractometer with Heat Controller; p. 1.
Author: Anton Paar K.G.; Title: A Universal Accessory for X-Ray Diffraction; p. 1.

Primary Examiner—Janice A. Howell
Assistant Examiner—Don Wong
Attorney, Agent, or Firm—Senniger, Powers, Leavitt & Roedel

[57] ABSTRACT

A specimen holder including a housing having a specimen chamber in it. A window defining a wall of the chamber allows transmission of at least a portion of the x-radiation from X-ray diffraction spectometry apparatus on which the holder is mounted, into the chamber. The housing has a passageway in it opening at one end into the specimen chamber and at the opposite end to outside the housing. A cylindrical specimen mount supports the specimen in the housing is constructed for sealing sliding reception in the passageway such that the specimen mount is rotatable about its longitudinal axis and movable lengthwise of the passageway while maintaining a seal with the passageway for positioning the specimen in the specimen chamber.

16 Claims, 1 Drawing Sheet

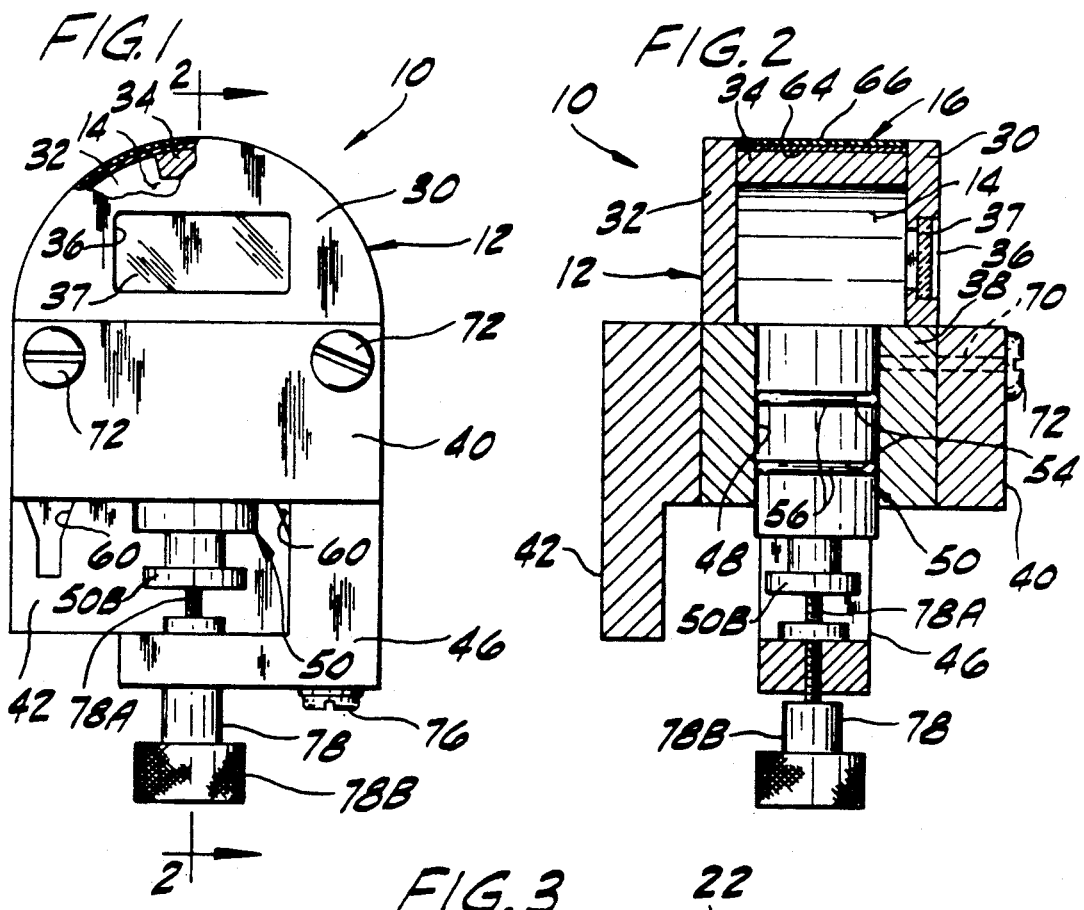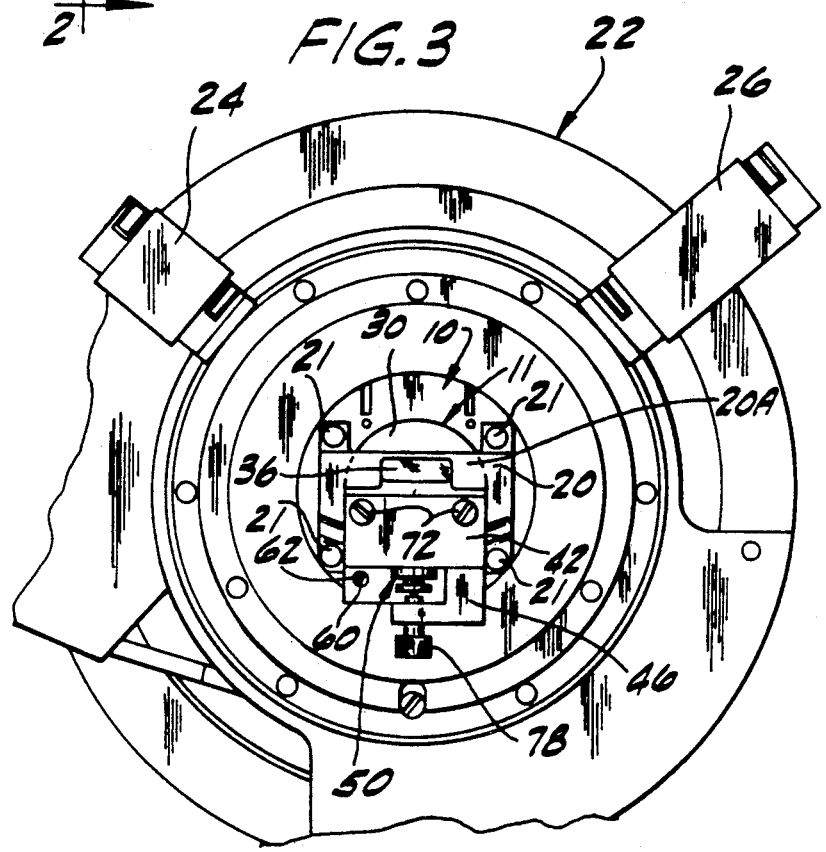

SPECIMEN HOLDER

BACKGROUND OF THE INVENTION

This invention relates generally to a specimen holder and more particularly to a specimen holder of the type used with an X-ray diffractometer or the like.

The study of structural properties of substances which are sensitive to air and/or moisture through X-ray diffraction spectrometry using a diffractometer or goniometer necessitates sealing enclosure of the substance prior to mounting on the diffractometer or goniometer. Enclosure of the substance in a capillary tube to protect it from air or moisture is unsatisfactory, particularly for the study of large surface area samples (e.g., samples having a surface area greater than about 2 to 3 square millimeters). The problem of crystallographic investigation of large surface area samples has become more acute with the increasing production of materials in the form of a thin film. Limited investigations of large surface area samples can be carried out using a small crystal or powder enclosed in a capillary tube with a full or half circle goniometer, which allows rotation of the capillary tube. However, full and half circle goniometers are expensive and simply not available to many researchers. In order to simulate large surface area geometry for study with a diffractometer, a researcher must engage in the arduous task of preparing and arranging a row of capillaries. Whether a full or half circle goniometer, or a diffractometer is used, the structural information which can be obtained is less complete than that which can be obtained through examination of a large surface area sample.

A large surface area sample may also be encased in an overlayer of mylar, or the like. However, at low angles of X-ray incidence on the sample, the mylar absorption of radiation (because of the increased thickness of mylar through which the radiation must pass) interferes with the readings obtained.

Vacuum tight specimen holders, which are typically used in high temperature studies, are presently available. These holders typically include a housing having a specimen holding chamber, one wall of which is defined by a hemi-cylindrical window made of material which transmit x-radiation from the diffractometer. The windows are typically made of aluminum or beryllium foil, which are suitably X-ray transmissive and temperature resistant, but which are relatively fragile. Moreover, these high temperature holders are large and cumbersome to handle and mount on a goniometer or diffractometer. Frequently, a substantial modification must be made to the diffractometer or goniometer in order to mount the holder. Disposition of an air or moisture sensitive sample in the housing is difficult because the sample must be transferred from a glove box or other air tight container to the holder. Moreover, a skilled researcher may spend an hour or more aligning the specimen before any data can be acquired.

SUMMARY OF THE INVENTION

Among the several objects and features of the present invention may be noted the provision of a specimen holder of the type used on X-ray diffraction spectrometry apparatus which is easily and quickly fitted onto existing X-ray diffraction spectrometry apparatus; the provision of such a specimen holder in which a specimen may be mounted while the holder is in a glove box; the provision of such a specimen holder which allows for positioning of the specimen from outside the holder; the provision of such a holder having a window for transmission of X-rays which absorbs undesired x-radiation given off by the apparatus; the provision of such a holder in which the window is of sturdy construction; and the provision of such a specimen holder which is inexpensive to manufacture and easy to use.

Generally, a specimen holder constructed according to the principles of the present invention comprises a housing having a specimen chamber therein. Window means defining a wall of the chamber is adapted to transmit at least a portion of the x-radiation from X-ray diffraction spectometry apparatus, on which the holder is mounted, into the chamber. The housing has a passageway therein opening at one end into the specimen chamber and at the opposite end to outside the housing. Means for supporting the specimen in the housing is adapted for sealing sliding reception in the passageway such that said support means is rotatable about its longitudinal axis and movable lengthwise of the passageway while maintaining a seal with the passageway for positioning the specimen in the specimen chamber.

Other objects and features of the present invention will be in part apparent and in part pointed out hereinafter.

BRIEF DESCRIPTION OF THE DRAWINGS

FIG. 1 is a front elevation of a specimen holder of the present invention with parts broken away to show detail;

FIG. 2 is a section taken in the plane including line 2—2 of FIG. 1; and

FIG. 3 is a fragmentary elevation showing the specimen holder as mounted on a goniometer.

Corresponding reference characters indicate corresponding parts throughout the several views of the drawings.

DETAILED DESCRIPTION OF THE PREFERRED EMBODIMENT

Referring now to the drawings, a specimen holder of the present invention, indicated generally by reference numeral 10, is shown to comprise a housing 12 having a specimen chamber 14 within, and a hemi-cylindrical window 16 defining one wall of the chamber. The specimen holder 10 is constructed for mounting on a bracket 20 of X-ray diffraction spectrometry apparatus such as the goniometer 22 illustrated in FIG. 3, which is the D500 goniometer manufactured by Seimens Analytical X-Ray Instrument, Inc. of Germany, having a headquarters in this country in Madison, Wis. However, it is to be understood that the specimen holder 10 of the present invention may be used with other goniometers and diffractometers. The goniometer 22 has an X-ray source 24 which and emits X-rays generally toward the center of the goniometer, where the specimen is supported by the bracket 20. The goniometer 22 further includes an X-ray detector 26 generally at the opposite side, which detects the diffracted X-rays from the specimen. The goniometer 22 is sold with the bracket 20 which is suitable for supporting specimen holders of the type for holding samples which are not sensitive to air or moisture. As described more fully below, the specimen holder 10 of the present invention is adapted to be supported on this same bracket 20.

The specimen chamber 14, which is hemi-cylindrical in shape, is defined by the window 16 at the top of the chamber, a semi-circular front wall 30 and a semi-circular rear wall 32. A window support member 34 extends between and is mounted at opposing ends on the front and rear walls 30, 32 of the chamber 14. It is envisioned that the window 16 may be supported on the front and rear walls without window support member 34. The front wall 30 has a viewport 36 closed by a glass panel 37 which allows visual inspection of the location of the specimen within the chamber 14. Beneath the specimen chamber 14 is the body of the housing 12, which forms the floor of the chamber. The body includes a central block 38 on which is mounted in a suitable fashion, such as by welding, the front wall 30, the rear wall 32, a front plate 40, and a rear or mounting plate 42. An L-shaped Positioning arm 46 is removably mounted on the underside of the central block 38. The central block 38 is bored through to form a passageway 48 opening at one end into the specimen chamber 14 and at the opposite end to the outside. The front and rear walls 30, 32, window support 34, central block 38, positioning arm 42, front plate 40, and mounting plate 42 are constructed of a strong, lightweight material, such as aluminum.

The specimen to be studied (not shown) is supported in the chamber by a piston (broadly "support means"), indicated generally at 50, sized for a close, sliding fit in the passageway 48 in the central block 38. The piston 50 has two axially spaced, circumferentially extending grooves 54 in which are received O-rings 56. The O-rings 56 engage the wall of the passageway 48 upon insertion of the piston 50 for sealing between the piston and the passageway so as to block fluid communication between the specimen chamber 14 and the outside through the passageway. The O-rings 56 are adapted for sliding over the passageway wall while remaining sealed with the wall. This allows the piston 50 to be moved longitudinally in the passageway 48, and to be rotated about its axis without breaking the seal. The piston 50 has a cylindrical upper portion 50A and a knob-shaped lower portion 50B, which facilitates gripping the piston for moving the piston. A flat upper surface 50C of the piston supports the specimen to be studied.

The specimen holder 10 may be mounted on the goniometer 22 by inserting it into the bracket 20 already provided on the goniometer. The bracket 20 is attached to the goniometer 22 by bolts 21, and includes an outwardly projecting, cantilevered support 20A. The specimen holder 10 is receivable between the bracket support 20A and the goniometer 22. The mounting plate 42 of the housing 12 has two generally Y-shaped openings 60 in it which are aligned with threaded bolt holes (not shown) in the goniometer 22. Mounting bolts 62 (only one is shown) are received through these openings and into the bolt holes to secure the specimen 10 holder onto the goniometer 22. Once mounted on the goniometer 22, no further movement of the housing 12 is required in order to properly align the specimen inside for incidence with the X-ray beam emitted by the goniometer. Lateral and front-to-back alignment of the specimen are already achieved by the mounting of the specimen holder 10 in the bracket 20. Vertical alignment and rotational positioning is accomplished by moving the piston 50 in the passageway. The orientation of the specimen in the specimen holding chamber 14 may be observed through the viewport 36.

The hemi-cylindrical window 16 allows the angle of incidence of the X-rays on the specimen to be varied substantially through 90° with no variation in the amount of x-radiation absorbed by the window. The window 16 also has a sturdy two-ply construction. The inner layer is a thin (e.g., $6 \times 10^{-6}$ m) sheet 64 of nickel foil which absorbs approximately 95% of $K_B$ X-rays and white radiation produced by the copper filament in the cathode ray tube (not shown) of the goniometer 22. Copper filaments are the most commonly used filament in diffractometers and goniometers. $K_B$ X-rays and white radiation are undesirable for purposes of gathering crystallographic data from specimens, because the spectrum produced by the diffracted rays is too complex for analysis. A monochromatic x-ray beam is necessary. However, it is to be understood that when filaments of different materials are used (e.g., cobalt) then a different filtering foil would be used (e.g., iron). The thinness of the sheet 64 of nickel is necessary to produce sufficient transmissivity to x-radiation from the goniometer 22. It has been found that the window 16 reduces the detected intensity of radiation in the specimen chamber 14 by about 40%. The outer layer 66 of the window is made of a stronger material such as aluminized polyethylene glycol terephtalate film (sold under the registered trademark "Mylar" by E.I. duPont de Nemours & Company mylar which provides protection and support for the nickel foil sheet 64. The window 16 is attached to the central block 38, front and rear walls of the chamber 30, 32, and window support 34 by suitable means such as by gluing, or by the use of arcuate bands (not shown) which may be attached by screws (not shown) to the housing over the front and rear edge margins of the window. The advantage of the latter attachment configuration being the ease with which a damaged window may be removed and replaced. In either case, the window is attached to the housing so as to seal with the housing, and it has been found that the nickel foil sheet 64 facilitates sealing. Windows made only of aluminized mylar are not air tight.

Two gas ports 70 in the housing are provided so that an inert gas may be circulated through the specimen chamber to protect the specimen if desired. The gas ports 70 extend through the front plate 40 and central blocks and open into the specimen chamber 14 on either side of the opening of the passageway 48 into the chamber. As shown in the drawings, the ports 70 have been sealed off by plugs 72.

In use, the specimen holder 10, which is small enough (approximately $2'' \times 2'' \times 1''$) to fit in the palm of the hand, may be placed in ordinary glove box (not shown) in which a vacuum pressure has been drawn and an inert gas (e.g., dry air, nitrogen or argon) has been used to flush out any remaining moist air which can damage an air or moisture sensitive material. The piston 50 is removed from the passageway in the housing prior to insertion in the glove box and one of the plugs 72 is removed from its gas port 70. The specimen is removed from its container and mounted on the flat upper surface 50C of the piston 50. The piston is then reinserted into the passageway 48 with the O-rings 56 engaging the walls of the passageway, sealing the specimen chamber 14 from communication through the passageway. Gas compressed by inertion of the piston 50 escapes through the open gas port 70 so that over-pressure in the specimen chamber 14 is avoided. Thus, a vacuum pressure and inert atmosphere is maintained in the specimen chamber 14 upon removal of the specimen holder 10 from the glove box.

After insertion of the specimen into the passageway 48 and re-stopping of the open gas port 70 with the plug 72, the holder 10 is removed from the glove box. The positioning arm 46, which is mounted on the central block 38 of the housing by a mounting screw 76, carries a locating screw 78 threadably mounted under the piston 50 in an opening through the laterally extending portion of the arm. The upper end 78A of the screw is engageable with the bottom lower portion 50B of the piston for precise control of the vertical position of the piston. The lower end 78B of the locating screw includes a knurled head to facilitate gripping. Rotation of the locating screw 78 in the appropriate direction allows the vertical position of the piston to be positively located at a lower or higher point. The specimen holder 10 is mounted on the bracket 20 of the goniometer 22 in the fashion described above. The piston 50 is initially positioned so that the specimen is approximately flush with the floor of the specimen chamber 14. Alignment of the specimen then is made by raising the piston 50 using the locating screw 78, until proper alignment is achieved (i.e., when the X-rays from the goniometer 22 are incident on the specimen). Alignment may also be carried out by rotation of the piston 50. The rotational alignment feature is particularly useful when a specimen, such as a single crystal, requires a precise orientation before readings may be taken. Data may then be collected from the specimen. In some instances, additional crystallographic information about the specimen may be quickly and easily acquired by rotating the specimen and taking another set of data.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A specimen holder for use on X-ray diffraction spectrometry apparatus, the holder comprising a housing having a specimen chamber therein and window means defining a wall of the chamber, said window means being capable of transmitting at least a portion of the x-radiation from the diffraction apparatus into the chamber and transmitting at least a portion of the x-radiation refracted from a specimen in the chamber to a detector, the housing having a generally vertically extending passageway therein opening at an upper end into the specimen chamber and at a lower end to outside the housing, support means including an upper surface for supporting the specimen in the housing, said support means being capable of slidably sealing reception in the passageway such that said support means is rotatable about its longitudinal axis and movable lengthwise of the passageway while maintaining a seal with the passageway for positioning the specimen in the specimen chamber.

2. A specimen holder as set forth in claim 1 wherein said support means is capable of being moved from outside the housing.

3. A specimen holder as set forth in claim 2 wherein the housing further comprises a port for viewing the specimen in the specimen chamber.

4. A specimen holder as set forth in claim 1 further comprising locating means mounted on the housing and engageable with said support means for holding said support means in a predetermined vertical position in the passageway, said locating means being adjustable vertically thereby to change the vertical location of said support means in the passageway and the vertical position of the specimen in the specimen chamber.

5. A specimen holder as set forth in claim 4 wherein the specimen chamber is airtight, and wherein said support means comprises a piston member and sealing means on the piston member adapted for engagement with walls of the passageway thereby to seal the passageway with the body.

6. A specimen holder as set forth in claim 1 wherein said window means capable of absorbing at least about 90 percent of $K_B$ X-rays from the diffraction apparatus.

7. A specimen holder as set forth in claim 6 wherein said window means comprises a window of two layer construction including an inner layer of nickel foil and an outer layer.

8. A specimen holder as set forth in claim 7 wherein the outer layer is made of aluminized polyethylene glycol terephtalate film.

9. A specimen holder for use on X-ray diffraction spectrometry apparatus, the holder comprising a housing having a specimen chamber therein and a window defining a wall of the chamber capable of transmitting x-radiation from the diffraction apparatus into the chamber, the housing having a generally vertically extending passageway, the window being capable of absorbing at least about 90 percent of $K_B$ X-rays from the diffraction apparatus, and means for rotatably supporting the specimen in the housing wherein said supporting means being capable of slidably sealing reception in the passageway.

10. A specimen holder as set forth in claim 9 wherein said window means comprises a window of two layer construction including an inner layer of nickel foil and an outer layer.

11. A specimen holder as set forth in claim 10 wherein the outer layer is made of aluminized polyethylene glycol terephtalate film.

12. A specimen holder as set forth in claim 11 wherein the layer of nickel foil has a thickness of approximately $6 \times 10^{-6}$ meters.

13. A specimen holder as set forth in claim 10 wherein the housing further comprises a port for viewing the specimen in the specimen chamber.

14. A specimen holder as set forth in claim 13 wherein said generally vertically extending passageway communicating at an upper end with the specimen chamber, and opening to the outside at a lower end, said support means being configured for sliding reception in said opening.

15. A specimen holder as set forth in claim 14 further comprising locating means mounted on the housing and engageable with said support means for holding said support means in a predetermined vertical position in the passageway, said locating means being adjustable vertically thereby to change the vertical location of said support means in the passageway and the vertical position of the specimen in the specimen chamber.

16. A specimen holder as set forth in claim 14 wherein the specimen chamber is airtight, and wherein said support means comprises a piston member and sealing means on the piston member adapted for engagement with walls of the passageway thereby to seal the passageway with the body, said piston member being capable of rotational and translational movement in the passageway while remaining sealed with the housing.

* * * * *